US007994192B2

(12) United States Patent
Guiles et al.

(10) Patent No.: US 7,994,192 B2
(45) Date of Patent: *Aug. 9, 2011

(54) SUBSTITUTED THIENOPYRIDONE COMPOUNDS WITH ANTIBACTERIAL ACTIVITY

(75) Inventors: Joseph Guiles, Lafayette, CO (US); Xicheng Sun, Superior, CO (US); Nebojsa Janjic, Boulder, CO (US); Sarah Strong, Louisville, CO (US)

(73) Assignee: Crestone, Inc., Boulder, CO (US)

( * ) Notice: Subject to any disclaimer, the term of this patent is extended or adjusted under 35 U.S.C. 154(b) by 754 days.

This patent is subject to a terminal disclaimer.

(21) Appl. No.: 11/853,314

(22) Filed: Sep. 11, 2007

(65) Prior Publication Data
US 2008/0146609 A1 Jun. 19, 2008

Related U.S. Application Data

(60) Provisional application No. 60/826,945, filed on Sep. 26, 2006.

(51) Int. Cl.
| | |
|---|---|
| *A01N 43/42* | (2006.01) |
| *A61K 31/44* | (2006.01) |
| *A61K 31/47* | (2006.01) |
| *C07D 491/02* | (2006.01) |
| *C07D 498/02* | (2006.01) |
| *C07D 471/02* | (2006.01) |
| *C07D 515/02* | (2006.01) |
| *C07D 215/00* | (2006.01) |

(52) U.S. Cl. ......... 514/310; 514/312; 546/114; 546/153
(58) Field of Classification Search .................. 514/301, 514/312, 310; 546/114, 153
See application file for complete search history.

(56) References Cited

U.S. PATENT DOCUMENTS

| 4,710,506 A | 12/1987 | Davies et al. |
| 6,943,175 B2 | 9/2005 | Berge et al. |
| 7,030,137 B2 | 4/2006 | Berge et al. |
| 7,220,757 B2 | 5/2007 | Berge et al. |
| 2008/0108651 A1 | 5/2008 | Guiles et al. |
| 2008/0227808 A1 | 9/2008 | Guiles et al. |
| 2009/0163536 A1 | 6/2009 | Guiles et al. |

FOREIGN PATENT DOCUMENTS

| EP | 97300317.1 | 1/1997 |
| WO | WO 99/55677 | 11/1999 |
| WO | WO 00/21949 | 4/2000 |
| WO | WO 00/71524 | * 11/2000 |
| WO | WO 2004/052288 | 6/2004 |
| WO | WO 2004/069196 | 8/2004 |
| WO | WO 2004/078119 | 9/2004 |
| WO | WO 2008/039639 | 4/2008 |
| WO | WO 2008/039640 | 4/2008 |
| WO | WO 2008/039641 | 4/2008 |
| WO | WO 2008/039642 | 4/2008 |

OTHER PUBLICATIONS

Kim et al. (Bioorganic & Medicinal Chemistry (2003), 11(24), 5325-5331).*
Barker (1995) Synthetic Comm. 25:3729-3734.
Bartlett & Perl, (2005) N. Engl. J Med. 353:2503-2505.
Clabots et al. (1992) J Infect. Dis. 166:561-567.
Fleischmann et al. (1995) Science 269:496-512.
Jarvest et al. (2004) Bioorg. & Med. Chem. Lett. 14:3937-3941.
McFarland et al. (1989) N. Engl. J Med. 320:204-210.
Bartlett et al (1978) "Role of *Clostridium difficile* in Antibiotic-Associated *Pseudomembranous colitis*" Gastroenterology 75(5):778-782.
Critchley et al (2005) "Antibacterial Activity of REP8839, a New Antibiotic for Topical Use" Antimicrobial Agents and Chemotherapy 49(10):4247-4252.
Hall and O'Toole (1935) "Intestinal Flora in Newborn Infants with Description of a New Pathogenic Anaerobe" American Journal of Diseases of Children 49:390-402.
Loo et al (2005) "A Predominantly Clonal Multi-Institutional Outbreak of *Clostridium Difficile*-Associated Diarrhea with High Morbidity and Mortality" New England Journal of Medicine 353:2442-2449.
Lyerly et al (1988) "*Clostridium difficile*: Its Disease and Toxins" Clinical Microbiology Reviews 1(1):1-18.
Pépin et al (2005) "Increasing Risk of Relapse After Treatment of *Clostridium difficile* Colitis in Quebec, Canada" Clin. Infect. Dis. 40:1591-1597.
Teasley et al (1983) "Prospective Randomised Trial of Metronidazole Versus Vancomycin for *Clostridium-difficile*-Associated Diarrhoea and Colitis" The Lancet 2:1043-104.
Thomas et al (2003) "Antibiotics and Hospital-Acquired *Clostridium difficile*-Associated Diarrhoea: a Systematic Review" Journal of Antimicrobial Chemotherapy 51:1339-135.
Voth and Ballard (2005) "*Clostridium-difficile* Toxins: Mechanism of Action and Role in Disease" Clinical Microbiology Reviews 18(2):247-16.
Wilcox and Spencer (1992) "Clostridium difficile Infection: Responses, Relapses and Re-Infections" Journal of Hospital Infection 22:85-92.
Gentry et al (2003) "Variable Sensitivity to Bacterial Methionyl-tRNA Synthetase inhibitors Reveals Subpopulations of *Streptococcus pneumoniae* with Two Distinct methionyl-tRNA Synthetase Genes" Antimicrobial Agents and Chemotherapy 47(6):1784-1789.
Jarvest et al (2002) "Nanomolar Inhibitors of *Staphylococcus aureus* Methionyl tRNA Synthetase with Potent Antibacterial Activity Against Gram-Positive Pathogens" Journal of Medicinal Chemistry 45(10):1959-1962.

(Continued)

*Primary Examiner* — Shengjun Wang
*Assistant Examiner* — Uma Ramachandran
(74) *Attorney, Agent, or Firm* — Swanson & Bratschun, L.L.C.

(57) ABSTRACT

Novel bicyclic heteroaromatic compounds are provided that are inhibitors of bacterial methionyl tRNA synthetase (MetRS). Compounds of the invention generally have a left hand side chroman group or left hand side tetrahydroquinoline group and a right hand side thienopyridone group. Also disclosed are methods for their preparation and their use in therapy as antibacterial agents, particularly as anti-*Clostridium difficile* agents.

6 Claims, No Drawings

OTHER PUBLICATIONS

EP Supplemental Search Report (Mar. 21, 2011) EP Application No. 07842226.8.

Brown et al (2003) "Horizontal Transfer of Drug-Resistant Aminoacyl-Transfer-RNA Synthesis of Anthrax and Gram-Positive Pathogens" EMBO Reports 4(7):692-698.

Elsayed and Zhang (2004) "Bacteremia Caused by *Clostrididum symbiosum*" J. Clin. Microbiology 42(9):4390-4392.

Hurdle et al (2005) "Prospects for Aminoacyl-tRNA Synthetase Inhibitors as New Antimicrobial Agents" Antimicrobial Agents and Chemotherapy 49(12):4821-4833.

Jarvest et al (2003) "Conformational Restriction of Methionyl tRNA Synthetase Inhibitors Leading to Analogues with Potent Inhibition and Excellent Gram-Positive Antibacterial Activity" Bioorganic & Medicinal Chemistry Letters 13:1265-126.

Jiang et al (2009) "*Clostridium glycolicum* Wound Infections: Case Reports and Review of the Literature" J. Clin. Microbiology 47(5):1599-160.

Kim and Lee (2003) "3-D-QSAR Study and Molecular Docking of Methionyl-tRNA Synthetase Inhibitors" Bioorganic & Medicinal Chemistry 11:5325-533.

King (1994) "Bioisosteres, Conformational Restriction, and Prodrugs-Case History: An Example of a Conformational Restriction Approach" Medicinal Chemistry: Principle and Practice:206-22.

Lin et al (2001) "Principles and Applications of Asymmetric Synthesis" Wiley-Interscience pp. 1-1.

Office Action mailed Nov. 24, 2010 with respect to U.S. Appl. No. 11/853,636.

Office Action mailed Sep. 23, 2010 with respect to U.S. Appl. No. 11/853,477.

Office Action mailed Sep. 15, 2010 with respect to U.S. Appl. No. 11/853,589.

Smith M.B., (2001) "The Cahn-Ingold-Prelog System" March J, March's Advanced Org. Chem., 5th ed., Wiley-Interscience, NY, p. 139-143.

Smith-Slatas et al (Mar. 27, 2006) "Clostridium Septicum Infections in Children: A Case Report and Review of the Literature" Pediatrics 117:e796-e805 (http:www.pediatrics.org/cgi/content/full/117/4/e796).

* cited by examiner

```
                         SEQUENCE LISTING

<160> NUMBER OF SEQ ID NOS: 2

<210> SEQ ID NO 1
<211> LENGTH: 33
<212> TYPE: DNA
<213> ORGANISM: Artificial
<220> FEATURE:
<223> OTHER INFORMATION: Primer

<400> SEQUENCE: 1
ctgcagagct agcaaaccga gtttttatgt aac                                  33

<210> SEQ ID NO 2
<211> LENGTH: 33
<212> TYPE: DNA
<213> ORGANISM: Artificial
<220> FEATURE:
<223> OTHER INFORMATION: Primer

<400> SEQUENCE: 2
ctttctaagc ttctactaac gaacctcgga tcc                                  33
```

US 7,994,192 B2

SUBSTITUTED THIENOPYRIDONE COMPOUNDS WITH ANTIBACTERIAL ACTIVITY

RELATED APPLICATIONS

This application claims the benefit under 35 U.S.C. §119, of U.S. Provisional Patent Application Ser. No. 60/826,945 entitled SUBSTITUTED THIENOPYRIDONE COMPOUNDS WITH ANTIBACTERIAL ACTIVITY, filed Sep. 26, 2006, and incorporated by reference herein in its entirety. This application is related to U.S. Patent Applications: ENANTIOMER COMPOUNDS WITH ANTIBACTERIAL ACTIVITY, Ser. No. 60/826,940, filed Sep. 26, 2006 and to corresponding U.S. non-provisional and PCT applications filed on Sep. 11, 2007; SUBSTITUTED PHENYLETHER-THIENOPYRIDONE COMPOUNDS WITH ANTIBACTERIAL ACTIVITY, Ser. No. 60/826,954 filed Sep. 26, 2006 and corresponding U.S. non-provisional and PCT applications filed on Sep. 11, 2007; and METHODS AND COMPOUNDS FOR TREATMENT OF CLOSTRIDIUM BASED INFECTION, Ser. No. 60/826,957, filed Sep. 26, 2006 and corresponding U.S. non-provisional and PCT applications filed on Sep. 11, 2007. The current application is also related to U.S. Pat. No. 6,943,175, filed Dec. 5, 2003, and U.S. Pat. No. 7,030,137, filed Feb. 27, 2004, and to U.S. patent application Ser. No. 10/729,416, filed Dec. 5, 2003 and 11/223,327, filed Sep. 9, 2005. Each of the above referenced applications and patents are incorporated by reference herein for all purposes.

TECHNICAL FIELD

The present invention relates to novel bicyclic heteroaromatic compounds having a left hand side including chroman or tetrahydroquinoline group and a right hand side thienopyridone group. The present invention also relates to the use of these compounds as inhibitors of bacterial methionyl tRNA synthetase (MetRS), to processes for their preparation and to their uses in therapy as antibacterial agents. In particular, the invention relates to these compounds as used in therapy for *Clostridium difficile* based infections.

BACKGROUND OF THE INVENTION

The search for antibacterial agents began in the late 1800s with the realization that "germs" caused human disease. Over the past century scientists have developed a variety of drugs useful in the targeting and inhibition of numerous bacterial strains. In particular, antibacterial agents known as antibiotics have been developed and are in common use throughout the industrialized world to treat most known bacterial infections. Originally, antibiotics like penicillin inhibited replication of bacteria by blocking the action of transpeptidase, an enzyme responsible for the building of bacterial cell walls. However, due to overuse and resistance adaptations of many bacterial strains, many antibiotics have lost some or all of their effectiveness at treating infection. A line of antibacterial agents that target new molecular growth mechanisms would be useful in avoidance of further enhancement of antibiotic resistance. One such target is tRNA synthetase.

tRNA synthetases are involved in protein biosynthesis so that inhibition thereof may be expected to lead to a cessation of cell growth. Thus, for instance, the compound mupirocin, produced by the organism *Pseudomonas fluorescents*, is an antibacterial agent and is used as the active ingredient in the product Bactroban®, marketed by GlaxoSmithKline. Mupirocin has been shown to be an inhibitor of the isoleucyl tRNA synthetase. Each tRNA synthetase represents a separate target for drug discovery. tRNA synthetase inhibitors which are selective for bacterial cells over mammalian cells are of considerable therapeutic interest as they have the potential to be used as antibacterial agents in the treatment of human disease.

The sequence of the tRNA synthetase genes in the Gram positive organism *S. aureus* have recently been determined (see, for instance, European Patent application no 97300317.1, SmithKline Beecham, for *S. aureus* MetRS), thereby assisting the process of identifying inhibitors. In addition, the sequence of tRNA synthetase genes in other pathogenic bacteria, for instance the Gram negative organism *H. influenzae*, has also been published (R. D. Fleischmann et al., Science, 269, 496-512, 1995).

Several compounds have recently been disclosed for their inhibitory activity toward methionyl tRNA synthetase (MetRS) and for their capacity as antibacterial agents. In particular, Jarvest et al. described various bicyclic heteroaromatic compounds that have shown MetRS inhibition. (Bioorg. & Med. Chem. Lett. 14 (2004) 3937-3941). In light of these findings there continues to be a need in the art to identify and utilize compounds that target MetRS and thereby provide new approaches for the treatment of infectious disease.

One particularly interesting bacterial target is the organism *Clostridium difficile* (*C. difficile*). *C. difficile* is becoming a more prevalent infectious agent, where one to three percent of healthy individuals are carriers of the organism. (Bartlett & Perl, N. Engl. J Med., 353, 2503-2505, 2005; Clabots et al., J Infect. Dis., 166, 561-567, 1992; McFarland et al., N. Engl. J Med., 320, 204-210, 1989). The risk of infection and disease becomes increasingly prevalent in the immunodeficient, elderly, and especially to the elderly in healthcare settings, e.g., nursing home, hospital, doctors office, etc. Few conventional antibacterial drugs have shown promise in the treatment of *C. difficile*, in fact only vancomycin is approved by the FDA for treatment of *C. difficile* associated diarrhea (CDAD) (*C. difficile* has shown surprising resistance to conventional antibiotic treatment, often flourishing in the gut of individuals under treatment). As such, there is a need in the art to obtain additional approaches for the treatment of *C. difficile* based infection, especially treatments that avoid conventional antibiotic treatments and therefore antibiotic resistance.

Against this backdrop the present invention has been discovered.

DETAILED DESCRIPTION OF THE INVENTION

We have now found a novel class of bicyclic heteroaromatic compounds that are potent inhibitors of bacterial MetRS. This new class of compounds is shown to have broad applicability as antibacterial agents for numerous Gram-positive and Gram-negative bacteria, and in particular is shown to be potent antibacterial agents for *C. difficile* based infection (MetRS inhibitors have best activity against Gram-positive organisms and far weaker activity against Gram-negative organisms).

In general, bicyclic heteroaromatic compounds of the invention have a left hand side (LHS) as shown in Formula 1 and a right hand side (RHS) thienopyridone group. In particular, the invention provides compounds of the formula (I):

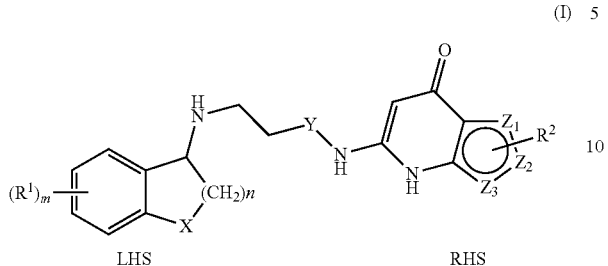

in which
R$^1$ is selected from halo, cyano, hydroxyl, (C$_{1-6}$)alkyl (optionally substituted by halo, hydroxyl, amino, mono to perfluoro(C$_{1-3}$)alkyl, carboxy, or (C$_{1-6}$)alkoxycarbonyl), (C$_{3-7}$) cycloalkyl, (C$_{1-6}$)alkoxy, amino, mono- or di-(C$_{1-6}$) alkylamino, acylamino, carboxy, (C$_{1-6}$)alkoxycarbonyl, carboxy(C$_{1-6}$)alkyloxyl, (C$_{1-6}$)alkylthio, (C$_{1-6}$)alkylsulphanyl, (C$_{1-6}$)alkylsulphonyl, sulphamoyl, mono- and di(C$_{1-6}$) alkylsulphamoyl, carbamoyl, mono- and di-(C$_{1-6}$)alkylcarbamoyl, and heterocyclyl;

Y is a linker group having from one to six methylene groups in a straight chain and in which one or more methylene groups may have one or more (C$_{1-6}$) alkyl, (C$_{1-6}$)alkoxy or (C$_{1-6}$)alkylidenyl substituents;

R$^2$ is selected from halo, cyano, hydroxyl, (C$_{1-6}$)alkyl (optionally substituted by halo, hydroxyl, amino, mono to perfluoro(C$_{1-3}$)alkyl, carboxy, or (C$_{1-6}$)alkoxycarbonyl), (C$_{3-7}$) cycloalkyl, (C$_{1-6}$)alkoxy, amino, mono- or di-(C$_{1-6}$) alkylamino, acylamino, carboxy, (C$_{1-6}$)alkoxycarbonyl, carboxy(C$_{1-6}$)alkyloxyl, (C$_{1-6}$)alkylthio, (C$_{1-6}$)alkylsulphanyl, (C$_{1-6}$)alkylsulphonyl, sulphamoyl, mono- and di(C$_{1-6}$) alkylsulphamoyl, carbamoyl, mono- and di-(C$_{1-6}$)alkylcarbamoyl, and heterocyclyl;

when $Z_1$ is S, $Z_2$ and $Z_3$ are CH; when $Z_2$ is S, $Z_1$ and $Z_3$ are CH; when $Z_3$ is S, $Z_1$ and $Z_2$ are CH;

X is NH, S, SO, SO$_2$, O or CH$_2$;

m is 0 or an integer from 1 to 4; and n is one, two or three.

In a preferred embodiment of the invention compounds having a left hand side chroman group and a right hand side thienopyridone group are provided, as shown in formula (II)

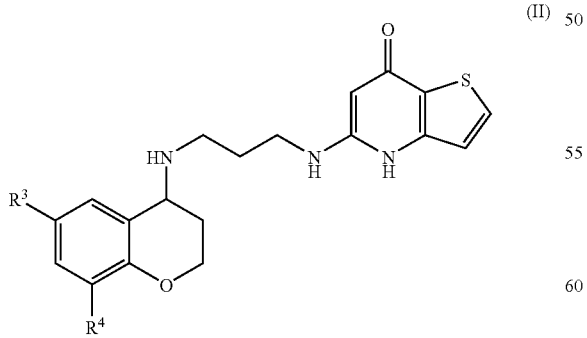

in which:
R$^3$ and R$^4$ can be the same or a different substituent and are as defined previously for R$^1$. In preferred embodiments, R$^3$ is a halogen and in most preferred embodiments R$^3$ is bromine, chlorine, or iodine. In preferred embodiments R$^4$ is a halogen or sulfane, and in most preferred embodiments R$^4$ is a bromine, chlorine, iodine or sulfane.

In another preferred embodiment of the invention, compounds having a left hand side tetrahydroquinoline group and right hand side thienopyridone group are disclosed and shown in formula (III):

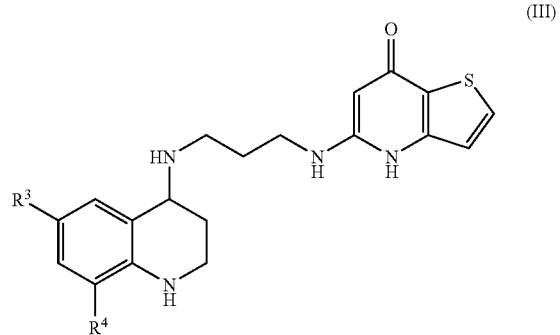

in which:
R$^3$ and R$^4$ can be the same or a different substituent and are as defined previously for R$^1$. In preferred embodiments, R$^3$ is a halogen and in most preferred embodiments R$^3$ is bromine, chlorine, or iodine. In preferred embodiments R$^4$ is a halogen or sulfane, and in most preferred embodiments R$^4$ is a bromine, chlorine, iodine or sulfane.

In another preferred embodiment of the invention, compounds having a left hand side benzothiopyran group and right hand side thienopyridone group are disclosed and shown in formula (IV):

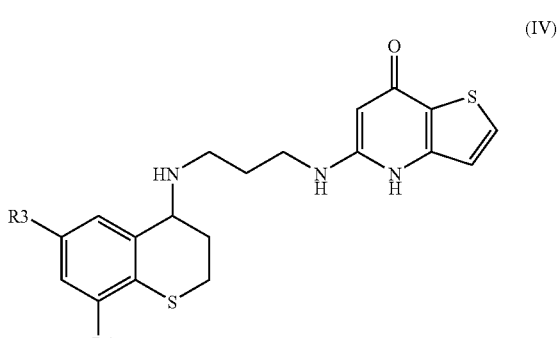

in which:
R$^3$ and R$^4$ can be the same or a different substituent and are as defined previously for R$^1$. In preferred embodiments, R$^3$ is a halogen and in most preferred embodiments R$^3$ is bromine, chlorine, or iodine. In preferred embodiments R$^4$ is a halogen or sulfane, and in most preferred embodiments R$^4$ is a bromine, chlorine, iodine or sulfane.

Compounds of formula (I)-(IV) are novel inhibitors of MetRS.

Salts may be formed from inorganic and organic acids. Representative examples of suitable inorganic and organic acids from which pharmaceutically acceptable salts of compounds of formulas (I)-(IV) may be formed include maleic, fumaric, benzoic, ascorbic, pamoic, succinic, bismethylenesalicylic, methanesulfonic, ethanedisulfonic, acetic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids.

When used herein, the term "alkyl" and similar terms such as "alkoxy" includes all straight chain and branched isomers. Representative examples thereof include methyl, ethyl, n-propyl, iso-propyl, n-butyl, sec-butyl, iso-butyl, t-butyl, n-pentyl and n-hexyl.

When used herein, the terms "alkenyl" and "alkynyl" include all straight chain and branched isomers. Representative examples thereof include vinyl, ethynyl and 1-propynyl.

Preferred substituents for alkyl and alkenyl groups include, for example, and unless otherwise defined, halogen, cyano, azido, nitro, carboxy, $(C_{1-6})$alkoxycarbonyl, carbamoyl, mono- or di-$(C_{1-6})$alkylcarbamoyl, sulpho, sulphamoyl, mono- or di-$(C_{1-6})$alkylsulphamoyl, amino, mono- or di-$(C_{1-6})$alkylamino, acylamino, ureido, $(C_{1-6})$alkoxycarbonylamino, 2,2,2-trichloroethoxycarbonylamino, aryl, heterocyclyl, hydroxyl, $(C_{1-6})$alkoxy, acyloxy, oxo, acyl, 2-thienoyl, $(C_{1-6})$alkylthio, $(C_{1-6})$alkylsulphinyl, $(C_{1-6})$alkylsulphonyl, hydroxyimino, $(C_{1-6})$alkoxyimino, hydrazino, hydrazono, benzohydroximoyl, guanidino, amidino and iminoalkylamino.

When used herein, the term "aryl" includes, unless otherwise defined, phenyl or naphthyl optionally substituted with up to five, preferably up to three substituents.

When substituted, an aryl group may have up to three substituents. Preferred substituents for an aryl group include, for example, and unless otherwise defined, halogen, cyano, $(C_{1-6})$alkyl, mono to perfluoro$(C_{1-3})$alkyl, $(C_{3-7})$cycloalkyl, $(C_{2-6})$alkenyl, $(C_{1-6})$alkoxy, $(C_{2-6})$alkenoxy, arylC$_{(1-6)}$alkoxy, halo$(C_{1-6})$alkyl, hydroxyl, amino, mono- or di-$(C_{1-6})$alkylamino, acylamino, nitro, carboxy, $(C_{1-6})$alkoxycarbonyl, $(C_{1-6})$alkenyloxycarbonyl, $(C_{1-6})$alkoxycarbonyl$(C_{1-6})$alkyl, carboxy$(C_{1-6})$alkyl, $(C_{1-6})$alkylcarbonyloxy, carboxy$(C_{1-6})$alkyloxy, $(C_{1-6})$alkoxycarbonyl$(C_{1-6})$alkoxy, $(C_{1-6})$alkylthio, $(C_{1-6})$alkylsulphinyl, $(C_{1-6})$alkylsulphonyl, sulphamoyl, mono- and di-$(C_{1-6})$-alkylsulphamoyl carbamoyl, mono- and di-$(C_{1-6})$alkylcarbamoyl, and heterocyclyl.

When used herein, the term "heteroaryl" includes single or fused rings comprising up to four hetero-atoms in the ring selected from oxygen, nitrogen and sulphur. Preferably the heteroaryl ring comprises from 4 to 7, preferably 5 to 6, ring atoms. A fused heteroaryl ring system may include carbocyclic rings and need only include one heterocyclic ring.

When used herein, the term "heterocyclyl" includes aromatic and non-aromatic single or fused rings comprising up to four hetero-atoms in the ring selected from oxygen, nitrogen and sulphur. Suitably the heterocyclic ring comprises from 4 to 7, preferably 5 to 6, ring atoms. A fused heterocyclic ring system may include carbocyclic rings and need only include one heterocyclic ring.

When substituted, a heteroaryl or a heterocyclyl group may have up to three substituents. Preferred substituents include those previously mentioned for an aryl group as well as oxo.

When used herein, the terms "halogen" and "halo" include fluorine, chlorine, bromine, and iodine and fluoro, chloro, bromo, and iodo, respectively.

The compounds of the present invention are suitably provided in substantially pure form, for example at least 50% pure, suitably at least 60% pure, advantageously at least 75% pure, preferably at least 85% pure, more preferably at least 95% pure, especially at least 98% pure. All percentages are calculated on a weight/weight basis. All impure or less pure forms of a compound according to the invention may, for example, be used in the preparation of more pure forms of the same compound or of a related compound (for example a corresponding derivative) suitable for pharmaceutical use.

It will be appreciated that certain compounds of the present invention may comprise one or more chiral centers so that compounds may exist as stereoisomers, including diastereoisomers and enantiomers. Embodiments of the invention cover all such stereoisomers, and mixtures thereof, including racemates and mixtures having an enantiomeric excess of one of the enantiomers.

Accordingly, the present invention provides preferred compounds of the formula (V)-(XIII):

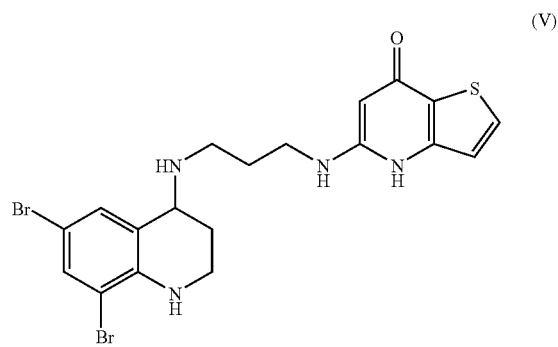

5-[3-(6,8-Dibromo-1,2,3,4-tetrahydro-quinolin-4-ylamino)-propylamino]-4H-thieno[3,2-b]pyridin-7-one;

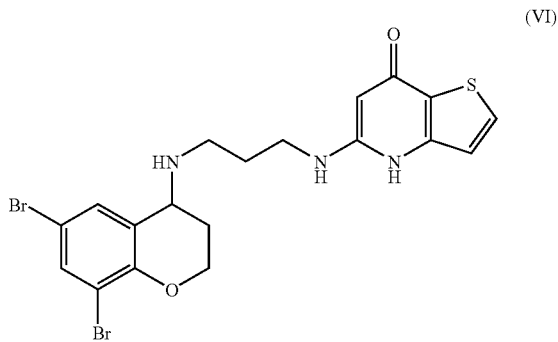

5-[3-(6,8-Dibromo-chroman-4-ylamino)-propylamino]-4H-thieno[3,2-b]pyridin-7-one;

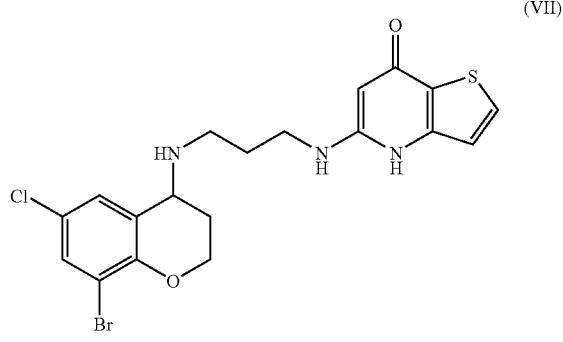

5-[3-(8-Bromo-6-chloro-chroman-4-ylamino)-propylamino]-4H-thieno[3,2-b]pyridin-7-one;

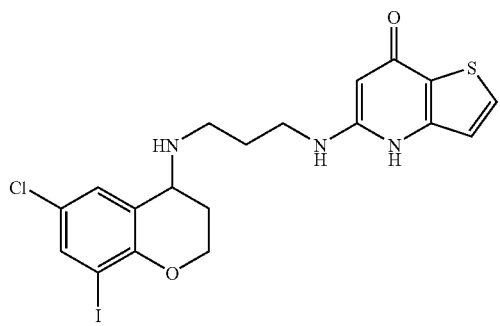

5-[3-(6-Chloro-8-iodo-chroman-4-ylamino)-propylamino]-4H-thieno[3,2-b]pyridin-7-one;

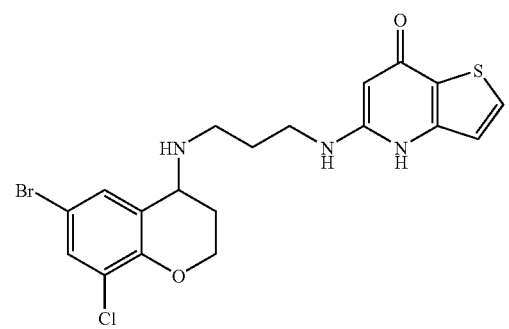

5-[3-(6-Bromo-8-chloro-chroman-4-ylamino)-propylamino]-4H-thieno[3,2-b]pyridin-7-one;

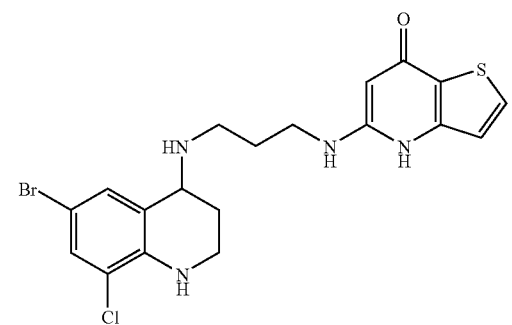

5-[3-(6-Bromo-8-chloro-1,2,3,4-tetrahydro-quinolin-4-ylamino)-propylamino]-4H-thieno[3,2-b]pyridin-7-one;

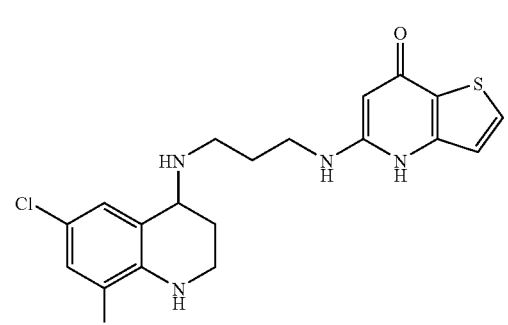

5-[3-(8-Bromo-6-chloro-1,2,3,4-tetrahydro-quinolin-4-ylamino)-propylamino]-4H-thieno[3,2-b]pyridin-7-one;

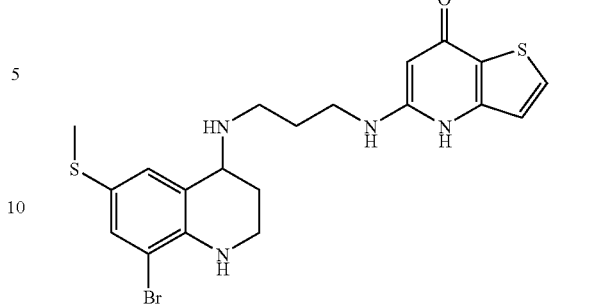

5-[3-(8-Bromo-6-methylsulfanyl-chroman-4-ylamino)-propylamino]-4H-thieno[3,2-b]pyridin-7-one;

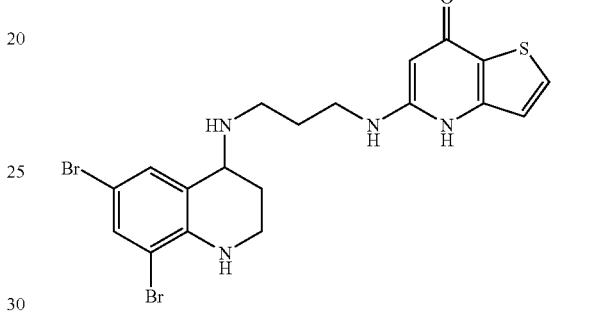

5-[3-(6-Bromo-8-fluoro-1,2,3,4-tetrahydro-quinolin-4-ylamino)-propylamino]-4H-thieno[3,2-b]pyridin-7-one; and

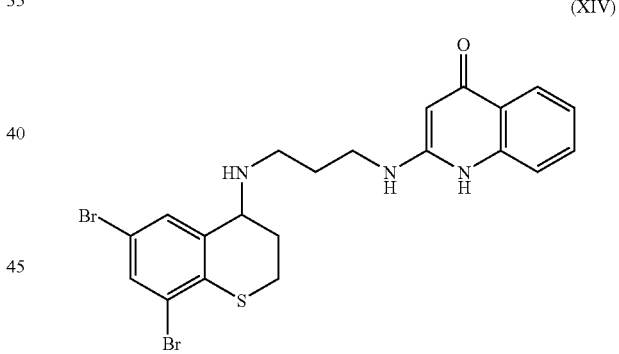

2-[3-(6,8-Dibromo-1-benzothiopyran-4-ylamino)-proplamino]-1H-quinolin-4-one.

The compounds of formulas (I)-(XIV) may be prepared by methods described herein or by methods described in the prior art that are incorporated by reference herein below. In addition, as described for formulas (I)-(IV), the compounds of formula (V)-(XIV) may be pharmaceutically acceptable salts.

In a first embodiment, an aniline compound of formula (XV, X=NH$_2$), (or other like compound) is dissolved in acetonitrile, and β-propionic lactone (n=2) is added. The mixture is stirred at reflux and then diluted with water and the pH elevated with base to pH 9. The mixture is extracted with dichloromethane and the aqueous layer separated and the pH lowered to approximately 5.0 with concentrated acid. The concomitant precipitate is collected on a sintered glass funnel and the cake washed with water until the filtrate reaches neutral pH. The solid is then dried under vacuum to yield the compound of formula (XVI) (phenylaminopropanoic acid).

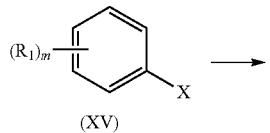

(XV)

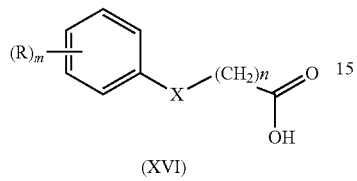

(XVI)

In an alternative embodiment, the compound of formula (XVI) can be prepared from a phenol (XV, X=OH) or thiophenol (XV, X=SH) and first dissolving it in base. The mixture is combined with β-propionic lactone (n=2) and the reaction heated at reflux. Once cooled and acidified to pH <4.0, the mixture is extracted with diethyl ether. The combined organic extracts are partitioned with brine, dried and evaporated to give the compound of formula (XVI, X=O or S, n=2, propanoic acid).

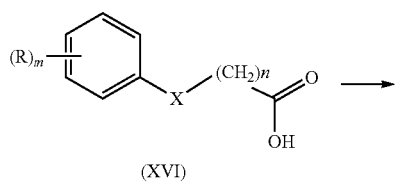

(XVI)

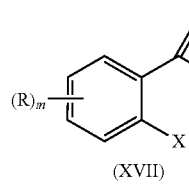

(XVII)

The compound of formula (XVI, X=NH, n=2)) is then added to a mixture of $P_2O_5$ and $H_3PO_4$ at 100° C. The mixture is stirred, with completion of the reaction determined by LC-MS. Once complete, the reaction is quenched with ice and the precipitate filtered, washed with water, and dried to give an off-white solid of formula (XVII, X=NH, n=2). In an alternative embodiment, a phenoxypropanoic acid (XVI, X=O, or S, n=2) is dissolved in benzene and $P_2O_5$ is added. The mixture is refluxed until complete and then cooled to ambient temperature. The benzene is decanted off and the residue is quenched with ice water. The mixture is extracted with diethyl ether and the combined organic extracts are partitioned with saturated sodium bicarbonate and dried over sodium sulfate, then filtered and evaporated to dryness in vacuo. The residue is purified by column chromatography to give a compound of formula (XVII, X=O or S, n=2).

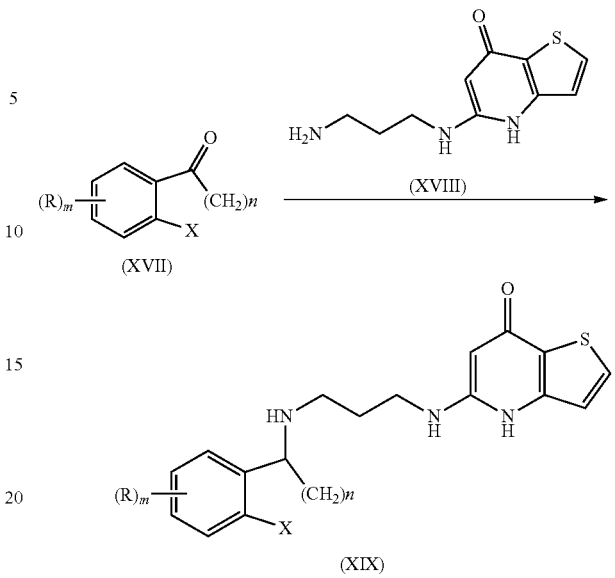

A compound having the formula (XIX) can be prepared as shown generally above by reacting a compound of formula (XVIII) (synthesis described in Example section) with a compound of formula (XVII) under reductive alkylation conditions. Specific examples of the procedure are described below in Example 1.

The compounds of this invention are active against a range of important pathogenic bacteria, including Gram positive organisms, such as *Staphylococci*, for instance *S. aureus*, Oxford and coagulase negative strains of *Staphylococci* such as *S. epidermidis*; *Streptococci*, for instance *S. pyogenes* ATCC19615 and *S. pneumoniae* R6; *Clostridium*, for instance *C. difficile*, and *Enterococci*, for instance *E. faecalis* 1 and *E. faecium*. Preferably, compounds of this invention are also active against Gram negative organisms, such as *Haemophilus*, for instance *H. influenzae* Q1; *Moraxella*, for instance *M. catarrhalis* 1502; *Helicobacter*, for instance *H. pylori* ATCC700824 and *Escherichia*, for instance *E. coli* DC0. The most preferred compounds of the present invention will be active against the organisms *C. difficile, S. aureus, S. pneumoniae, E. faecalis, E. faecium, H. influenzae*, and *M. catarrhalis* and *H. pylori*.

In addition, compounds of this invention are active against *Staphylococci* organisms such as *S. aureus* and coagulase negative strains of *Staphylocci* such as *S. epidermidis* which are resistant (including multiply-resistant) to other antibacterial agents, for instance, β-lactam antibiotics such as, for example, methicillin, macrolides, aminoglycosides, oxazolidinones, and lincosamides. Compounds of the present invention are therefore useful in the treatment of MRSA and MRCNS.

Compounds of the present invention are also active against strains of *E. faecalis* including vancomycin resistant strains and therefore of use in treating infections associated with VRE organisms. Furthermore, compounds of the present invention are useful in the treatment of *Staphylococci* organisms which are resistant to mupirocin.

Compounds of the invention are particularly potent, i.e., active, against strains of *Clostridium* including *C. difficile*. Therefore, compounds of the invention can be used to treat infections associated with *C. difficile*, e.g., pseudomembranous colitis, toxic megacolon, and other antibiotic associated diarrheas (AAD).

Compounds of the invention are not, however, active against mammalian cells. This provides an optimal combination of high activity against pathogenic bacteria and low or no activity against mammalian cells, allowing for the use of compounds of the invention in the treatment of mammals, and in particular humans.

Bacterial infections which may be treated include respiratory tract infections, otitis media, meningitis, endocarditis, skin and soft tissue infections in man, mastitis in cattle, and also respiratory infections in farm animals such as pigs and cattle. Accordingly, in a further aspect, the present invention provides a method of treating bacterial infection in human or non-human animals, which method comprises administering a therapeutically effective amount of a compound of formula (I)-(XIV) as hereinbefore defined, to a human or non-human animal in need of such therapy. It will be appreciated that a compound of the present invention which has a broad spectrum of antibacterial activity, including activity against both Gram positive and Gram negative bacteria will be of general use in the community for the empiric treatment of community acquired infections. In comparison, a compound of the present invention with a more limited spectrum, for instance activity against Gram positive bacteria, is more likely to be used in circumstances where the causative pathogenic organism has been identified.

The present invention provides a pharmaceutical composition comprising any of the compounds of formula (I)-(XIV) together with a pharmaceutically acceptable carrier or excipient.

The present invention further provides pharmaceutical compositions comprising combinations of compounds of formula (I)-(XIV) together with a pharmaceutically acceptable carrier or excipient. For example, a pharmaceutical composition of the invention can include a compound of formula (V) and a compound of formula (VII) in combination with the carrier or excipient.

The present invention also provides a method of treating bacterial infections in mammals, especially in humans and in domesticated animals, which comprises administering a compound of the invention, or a composition according to the invention, to a patient in need thereof.

The invention further provides the use of compounds of the invention in the preparation of a medicament composition for use in the treatment of bacterial infections.

The compounds and compositions according to the invention may be formulated for administration in any convenient way for use in human or veterinary medicine, by analogy with other antibiotics.

The compounds and compositions according to the invention may be formulated for administration by any route, for example oral, topical, parenteral, or rectal. The compositions may, for example, be made up in the form of tablets, capsules, powders, granules, lozenges, creams, suppositories, ointments, gels, lotions, syrups, or liquid preparations, for example solutions or suspensions, which may be formulated for oral use or in sterile form for parenteral administration by injection or infusion.

Tablets and capsules for oral administration may be in unit dosage form, and may contain conventional excipients including, for example, binding agents, for example, syrup, acacia, gelatin, sorbitol, tragacanth, or polyvinylpyrrolidone; fillers, for example lactose, sucrose, maize-starch, calcium phosphate, sorbitol or glycine; tabletting lubricants, for example magnesium stearate, talc, polyethylene glycol or silica; disintegrants, for example potato starch; and pharmaceutically acceptable wetting agents, for example sodium lauryl sulphate. The tablets may be coated according to methods well known in normal pharmaceutical practice.

Oral liquid preparations may be in the form of, for example, aqueous or oily suspensions, solutions, emulsions, syrups or elixirs, or may be presented as a dry product for reconstitution with water or another suitable vehicle before use. Such liquid preparations may contain conventional additives, including, for example, suspending agents, for example sorbitol, methyl cellulose, glucose syrup, gelatin, hydroxyethyl cellulose, carboxymethyl cellulose, aluminum stearate gel or hydrogenated edible fats; emulsifying agents, for example lecithin, sorbitan monooleate or acacia; non-aqueous vehicles (which may include edible oils), for example almond oil, oily esters (for example glycerine), propylene glycol, or ethyl alcohol; preservatives, for example methyl or propyl p-hydroxybenzoate or sorbic acid; and, if desired, conventional flavoring and color agents.

Compositions according to the invention intended for topical administration may, for example, be in the form of ointments, creams, lotions, eye ointments, eye drops, ear drops, impregnated dressings, and aerosols, and may contain appropriate conventional additives, including, for example, preservatives, solvents to assist drug penetration, and emollients in ointments, gels, and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

Compositions according to the invention may be formulated as suppositories, which may contain conventional suppository bases, for example cocoa-butter or other glycerides.

Compositions according to the invention intended for parenteral administration may conveniently be in fluid unit dosage forms, which may be prepared utilizing the compound and a sterile vehicle, water being preferred. The compound, depending on the vehicle and concentration used, may be either suspended or dissolved in the vehicle. In preparing solutions, the compound may be dissolved in water for injection and filter-sterilized before being filled into a suitable vial or ampoule, which is then sealed. Advantageously, conventional additives including, for example, local anesthetics, preservatives, and buffering agents can be dissolved in the vehicle. In order to enhance the stability of the solution, the composition may be frozen after being filled into the vial, and the water removed under vacuum; the resulting dry lyophilized powder may then be sealed in the vial and a accompanying vial of water for injection may be supplied to reconstitute the liquid prior to use. Parenteral suspensions may be prepared in substantially the same manner except that the compound is suspended in the vehicle instead of being dissolved and sterilization cannot be accomplished by filtration. The compound may instead be sterilized by exposure to ethylene oxide before being suspended in the sterile vehicle. Advantageously, a surfactant or wetting agent is included in such suspensions in order to facilitate uniform distribution of the compound.

A compound or composition according to the invention may suitably be administered to the patient in an antibacterially effective amount.

A composition according to the invention may suitably contain from 0.1% by weight, preferably from 10 to 60% by weight, of a compound according to the invention (based on the total weight of the composition), depending on the method of administration.

The compounds according to the invention may suitably be administered to the patient at a daily dosage of from 1.0 to 100 mg/kg of body weight. For an adult human (of approximately 70 kg body weight), from 50 to 3000 mg, for example about 1500 mg, of a compound according to the invention may be administered daily. Suitably, the dosage for adult humans is from 5 to 40 mg/kg per day. Higher or lower dosages may, however, be used in accordance with normal clinical practice.

When the compositions according to the invention are presented in unit dosage form, each unit dose may suitably comprise from 25 to 1000 mg, preferable from 50 to 500 mg, of a compound according to the invention.

Examples 13-18 below illustrate the potent antibacterial activity of the compounds of the present invention.

EXAMPLES

The following Examples are provided for illustrative purposes only and are not intended to limit the scope of the invention.

Example 1

Synthesis of Compounds of the Present Invention

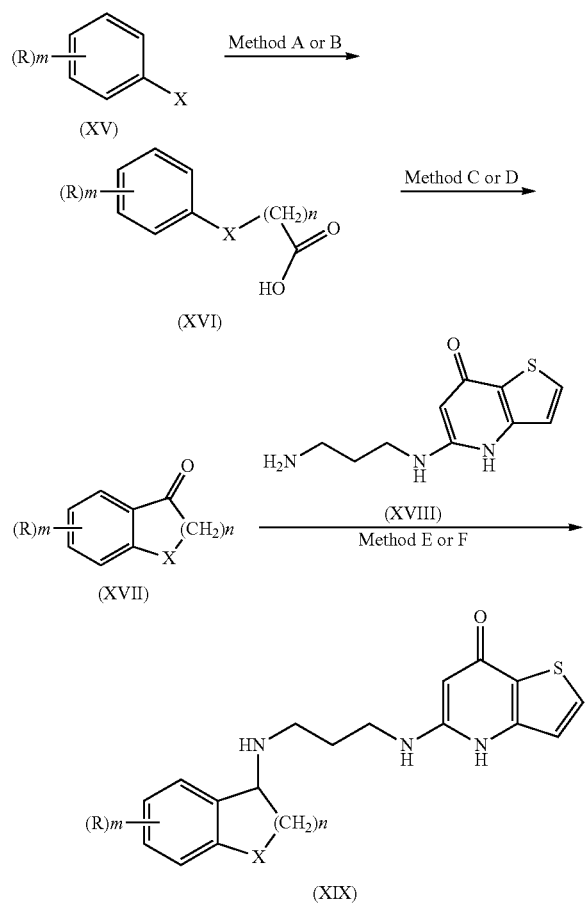

Method A: An aniline of formula (XV, X=NH$_2$, 30 mmol) was dissolved in acetonitrile and β-propionic lactone (one equivalent) was added. The mixture was stirred at reflux for 3 hours and then diluted with water and the pH elevated with sodium hydroxide to pH=9. The mixture was extracted with dichloromethane three times and the aqueous layer separated and the pH lowered to approximately 5.0 with concentrated HCl. The concomitant precipitate (formula XVI) was collected on a sintered glass funnel and the cake washed with water until the filtrated reaches neutral pH. The solid is then dried under vacuum to yield the compound of formula (XVI, X=NH, n=2).

Method B: A phenol or thiophenol of formula (XV, X=OH, or SH, 30 mmol) was dissolved in 2M aqueous sodium hydroxide (30 mmol). To the mixture, β-propionic lactone (30 mmol) was added and the reaction was refluxed for two hours. The reaction mixture was cooled to ambient temperature and acidified with HCl to pH <4 and extracted with diethyl ether. The combined organic extracts were extracted with saturated aqueous sodium bicarbonate. The basic aqueous layer was acidified to pH <4 and then extracted with ether. This ether extract was then partitioned with brine, dried over sodium sulfate, filtered and evaporated in vacuo to give an off-white solid of formula (XVI, X=O, or S, n=2).

Method C: A phenylaminopropanoic acid (formula XVI, X=NH, n=2, 2.0 mmol) was added to a mixture of P$_2$O$_5$ (15 g) and H$_3$PO$_4$ (6 ml) at 100° C. The mixture was stirred for two hours while maintaining the temperature. When the reaction was complete, as judged by LC-MS, the reaction was quenched with ice and the precipitate was filtered and washed with water and dried in vacuo to give an off-white solid of formula (XVII, X=NH, n=2).

Method D: A phenoxypropanoic acid (formula XVI, X=O, or S, n=2, 6.0 mmol) was dissolved in benzene and P$_2$O$_5$ was added. The mixture was refluxed for 2 hours and then cooled to ambient temperature. The benzene was decanted off and the residue was quenched with ice water. The mixture was extracted with diethyl ether three times and the combined organic extracts were partitioned with saturated sodium bicarbonate, and then dried over sodium sulfate, filtered, and evaporated to dryness in vacuo. The residue was purified by column chromatography, product eluted with a gradient of 0-20% ethyl acetate in hexanes, to give a white solid of formula (XVII, X=O, or S, n=2).

Method E: A representative example of method E is as follows. Preparation of 5-[3-(8-Bromo-6-chloro-1,2,3,4-tetrahydro-quinolin-4-ylamino)-propylamino]-4H-thieno[3,2-b]pyridin-7-one: A solution of 5-(3-Amino-propylamino)-4H-thieno[3,2-b]pyridine-7-one di-hydrochloride (XVIII) in methanol (0.08M) was prepared and then treated with sodium methoxide (2 equivalents, 0.5M in methanol). 8-Bromo-6-chloro-2,3-dihydro-1H-quinolin-4-one (1 equivalent) was added as a solid. Sodium cyanoborohydride (3 equivalents) was added as a solid. The mixture was then refluxed for 20 hours, adding an additional equivalent of sodium cyanoborohydride after 16 hours. The reaction mix was poured onto a column of silica gel and the product was eluted with 10% NH$_3$ (sat.)/MeOH and dichloromethane. Solvent was then removed in vacuo. Purification of the crude product was accomplished by flash chromatography, product eluted with a gradient of 0-12% NH$_3$ (sat.)/MeOH and dichloromethane. The resulting solid was triturated with ether, isolated by filtration, and dried to give the title compound as a white solid (formula XIX, X=NH).

Method F: A representative example of method F is as follows. Preparation of 5-[3-(6,8-Dibromo-chroman-4-ylamino)-propylamino]-4H-thieno[3,2-b]pyridin-7-one: A solution of 5-(3-Amino-propylamino)-4H-thieno[3,2-b]pyridin-7-one di-hydrochloride (XVIII) in methanol (0.125M) was prepared. This solution was treated with sodium methoxide (0.5M in methanol, 2 equivalents) and excess acetic acid (0.5 ml/mmol). 6,8-Dibromo-chroman-4-one (one equivalent) was added as a solid. The reaction was heated to reflux. Once a clear solution was obtained, the heat was removed and sodium cyanoborohydride (2 equivalents) was added as a solid. The mixture was then refluxed for 48 hours. The reaction mix was poured into water (6× the volume of methanol). The resulting solid was isolated by vacuum filtration through celite. The solid was then taken up in methanol and filtered to remove celite. Purification of the crude product was accomplished by flash chromatography, the product eluted with a gradient of 0-12% $NH_3$ (sat.)/MeOH and dichloromethane, to give the title compound as a white solid (formula XIX, X=O, or S).

Synthesis of compound XVIII, 5-(3-amino-propylamino)-4H-thieno[3,2-b]pyridine-7-one hydrochloride salt

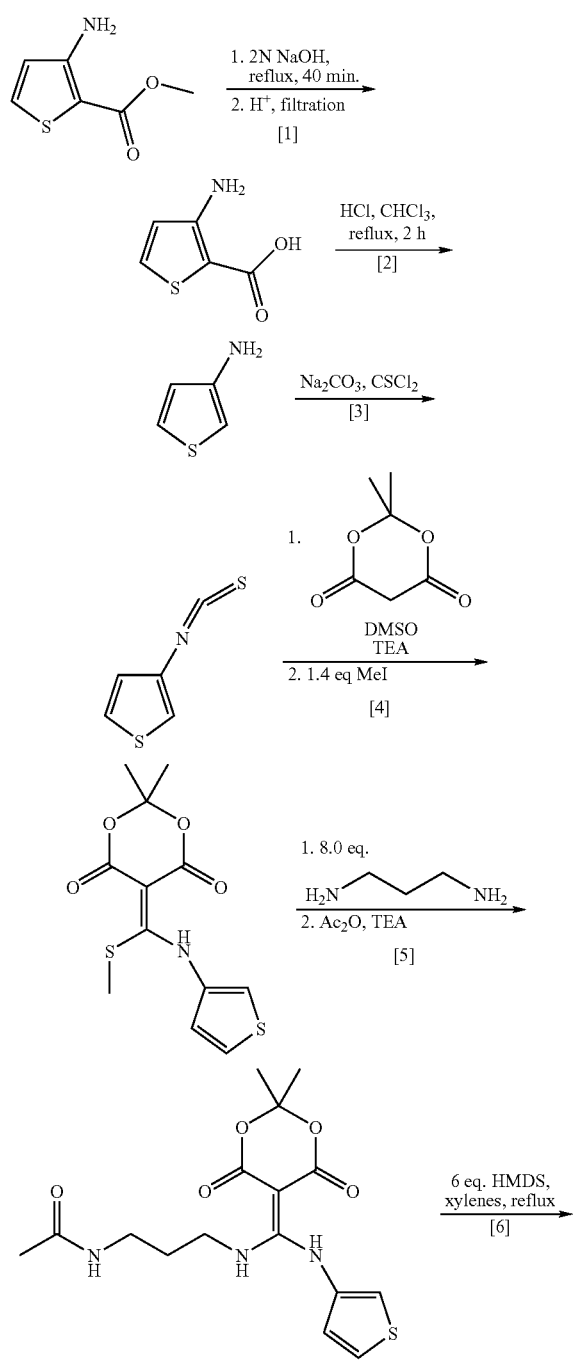

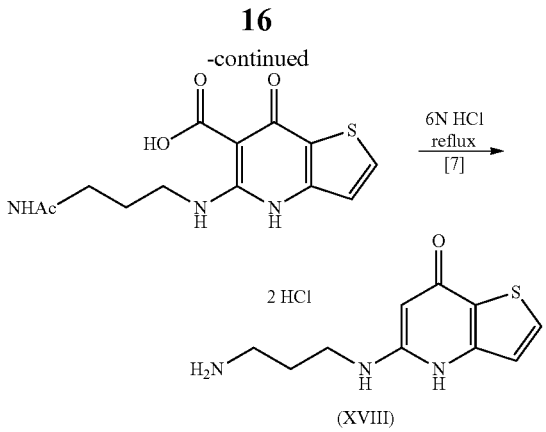

Step [1]: Methyl 3-aminothiophene-2-carboxylic ester (31 g, 0.197 mmol) was suspended in 2N NaOH (aq) (150 mL) and heated at reflux for 40 min. The resultant solution was cooled and acidified by conc. HCl to pH 2. The resultant slurry was filtered and left on the filter membrane with constant vacuum applied to the filter flask for an hour.

Step [2]: The wet cake of 3-Aminothiophene-2-carboxylic acid hydrochloride salt (Barker, J. M., et al. *Synthetic Comm.* 1995, 25, 3729-3734) was suspended in chloroform (300 mL) in the presence of concentrated hydrogen chloride (1 mL) and heated at reflux until all the starting material was consumed. The reaction was allowed to reach ambient temperature and the reaction solution was taken to the next step.

Step [3]: The resultant organic solution (see Step [2]) was treated with sodium carbonate (31 g) and water (100 mL) (pH: 8.0). The above biphasic solution was chilled with an ice bath and thiophosgene (19 mL, 0.236 mmol) was added dropwise with the reaction temperature controlled below 10° C. After the addition was complete, the reaction was stirred for 20 min. The organic layer was separated, partitioned with brine and dried over anhydrous sodium sulfate. After filtration and removal of solvent in vacuo, the mixture was purified by flash silica gel column, product eluted with ethyl acetate/hexane (1:4), to afford the desired product 3-thiophene isothiocynate (14 g, 50%) as dark oil. $^1$H NMR (CDCl$_3$): 7.27 (1H, m), 7.17 (1H, m), 6.98 (1H, d, J=5.2 MHz) ppm.

Step [4]: 3-Thiophene isothiocynate (14 g, 99 mmol) was treated with 2,2-dimethyl-1,3-dioxane-4,6-dione (15.7 g, 109 mmol) in dimethylsulfoxide (85 mL) in the presence of triethylamine (15.3 g, 109 mmol) and was stirred for 10 h. Then, the mixture was treated with iodomethane (14.78 g, 104 mmol) by slow addition over 2 h. The reaction end-point was checked by HPLC. Water (500 mL) was slowly added to the above mixture to precipitate the product. After filtration and drying under vacuum, 2,2-dimethyl-5-(methylsulfanyl-thiophene-3-ylamino-methylene)-[1,3]dioxane-4,6-dione was obtained (27.38 g, 94%) as a tan solid. $^1$H NMR (CDCl$_3$): 12.7 (1H, brs), 7.38 (1H, dd, J=3.2, 5 MHz), 7.25 (1H, d, J=3.2 MHz), 7.09 (1H, d, J=5), 2.38 (3H, s), 1.76 (6H, s) ppm.

Step [5]: A solution of 2,2-dimethyl-5-(methylsulfanyl-thiophene-3-ylamino-methylene)-[1,3]dioxane-4,6-dione (27.83 g, 92.8 mmol) in DCM/MeOH (4:1, 120 mL) was added to a solution of 1,3-diaminopropane (54.9 g, 138 mmol) in DCM/MeOH (4:1, 140 mL) (cooled in an ice bath) over one hour. The ice bath was removed after addition was complete. The reaction was stirred for 2 h at ambient temperature, then diluted with DCM (100 mL) and the resultant organic solution was washed with water (60 mL X 4) and brine (60 mL). Then, acetic anhydride (11 mL, 116 mmol) and trimethylamine (16 mL, 111.4 mmol) was added to the above organic solution and stirred for 30 min. An aqueous work-up with 1N HCl, then NaHCO$_3$ (saturated) and then brine was performed. The organic was dried with MgSO$_4$, filtered and volatile solvents removed in vacuo to afford the desired product N-(3-{[(2,2-dimethyl-4,6-dioxo-[1,3]dioxan-5-ylidene)-(thiophen-3-ylamnio)-ethyl]-amino}-propyl)-acetamide (30.7 g, 84%) as a brown oil, which was used in the next step without purification. $^1$H NMR (CDCl$_3$): 11.3 (1H, br s), 10.0 (1H, br s), 7.33 (1H, dd, J=3.2, 5 MHz), 7.07 (1H, d, J=3.2 MHz), 6.98 (1H, d, J=5), 3.20 (2H, quart, J 6.4 MHz), 3.90 (1H, quart. J=6.8 MHz), 1.94 (3H, s), 1.73 (6H, s), 1.68 (2H, m) ppm.

Step [6]: A solution of N-(3-{[(2,2-dimethyl-4,6-dioxo-[1,3]dioxan-5-ylidene)-(thiophen-3-ylamnio)-methyl]-amino}-propyl)-acetamide (30.65 g, 83.5 mmol) and hexamethyldisilazane (40.4, 251 mmol) in xylenes (150 mL) was heated at reflux for 4 h, and then concentrated to dryness. The resultant oil was carefully treated with methanol (20 mL). Methanol was removed to give a solid as the desired product 5-(3-acetamide-propylamino)-6-carboxyl-4H-thieno[3,2-b]pyridine-7-one. $^1$H NMR (D$_6$-DMSO): 11.9 (1H, br s), 9.91 (1H, br s), 8.04 (1H, d, J=4.8 MHz), 7.90 (1H, br s), 7.27 (1H, d, J=4.8 MHz), 3.41 (1H, quart. J=6.0 MHz), 3.20 (2H, quart, J 6.0 MHz), 1.78 (3H, s), 1.74 (2H, m) ppm Step [7]: 5-(3-acetamide-propylamino)-6-carboxyl-4H-thieno[3,2-b]pyridine-7-one (crude from Step [6]) was suspended in 6 N HCl (200 mL) and heated at reflux for 16 h. After the aqueous solution was evaporated in vacuo, the resultant salts were dissolved in ethanol/water (85:15, 100 mL), and heated at reflux with charcoal for 20 min. Then, filtration afforded a brown solution, and ethyl acetate (400 mL) was added to the solution to precipitate the desired product. Filtration and rinsing with ethyl acetate afforded the final pure product (23.8 g, 96%) as a tan solid. $^1$H NMR (D$_2$O) for 5-(3-amino-propylamino)-4H-thieno[3,2-b]pyridine-7-one hydrochloride salt (XVI): 7.77 (1H, d, J=5.6 MHz), 7.14 (1H, d, J=5.6 MHz), 3.35 (1H, t. J=6.4 MHz), 3.13 (2H, t, J=7.6 MHz), 2.03 (2H, m) ppm.

Example 2

Preparation of 5-[3-(6,8-Dibromo-1,2,3,4-tetrahydro-quinolin-4-ylamino)-propylamino]-4H-thieno[3,2-b]pyridin-7-one Following the general synthesis procedure described in Example 1 the following compound was prepared. Spectral data confirms the identity of the compound.

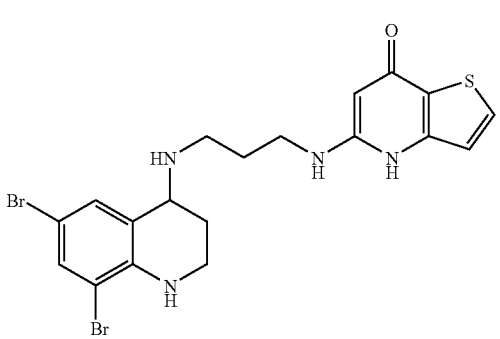

(V)

$^1$H NMR (400 MHz, CD$_3$OD): δ7.69 (d, 1H), 7.39 (d, 1H), 7.25 (d, 1H), 7.03 (d, 1H), 5.57 (s, 1H), 3.81 (t, 1H), 3.33-3.39 (m, 3H), 2.82 (m, 2H), 2.00-2.10 (m, 1H), 1.87 (m, 4H). MS (ES+): M/Z 512 (M+1).

Example 3

Preparation of 5-[3-(6,8-Dibromo-chroman-4-ylamino)-propylamino]-4H-thieno[3,2-b]pyridin-7-one Following the general synthesis procedure described in Example 1 the following compound was prepared. Spectral data confirms the identity of the compound.

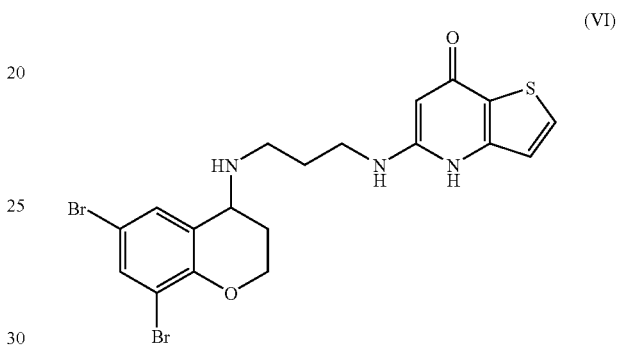

(VI)

$^1$H NMR (400 MHz, CD$_3$OD): δ 7.69 (d, 1H), 7.53 (s, 1H), 7.48 (s, 1H), 7.04 (d, 1H), 5.57 (s, 1H), 4.38 (m, 1H), 4.24 (m, 1H), 3.84 (t, 1H), 3.34 (t, 2H), 2.79 (m, 2H), 2.03 (m, 2H), 1.86 (m, 2H). MS (ES+): M/Z 514 (M+1).

Example 4

Preparation of 5-[3-(8-Bromo-6-chloro-chroman-4-ylamino)-propylamino]-4H-thieno[3,2-b]pyridin-7-one Following the general synthesis procedure described in Example 1 the following compound was prepared. Spectral data confirms the identity of the compound.

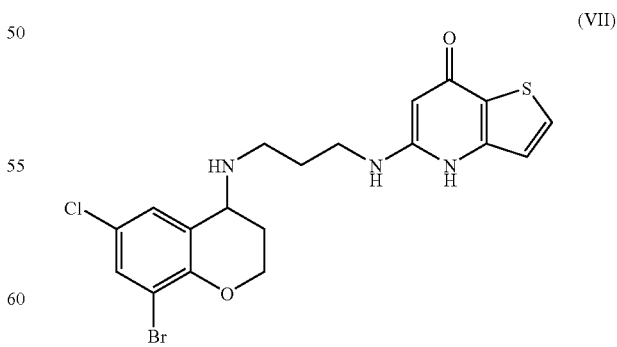

(VII)

$^1$H NMR (400 MHz, CD$_3$OD): δ 7.69 (d, 1H), 7.42 (d, 1H), 7.36 (d, 1H), 7.03 (d, 1H), 5.57 (s, 1H), 4.38 (m, 1H), 4.30 (m, 1H), 3.91 (t, 1H), 3.35 (t, 2H), 2.84 (m, 2H), 2.07 (m, 2H), 1.88 (m, 2H). MS (ES+): M/Z 470 (M+1).

Example 5

Preparation of 5-[3-(6-Chloro-8-iodo-chroman-4-ylamino)-propylamino]-4H-thieno[3,2-b]pyridin-7-one Following the general synthesis procedure described in Example 1 the following compound was prepared. Spectral data confirms the identity of the compound.

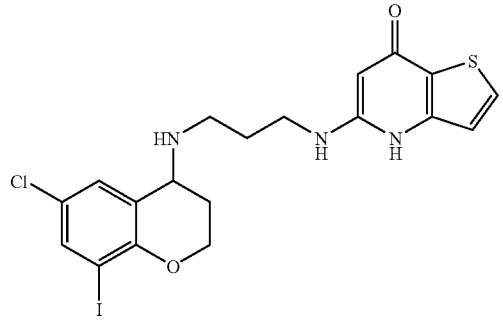

(VIII)

$^1$H NMR (400 MHz, CD$_3$OD): δ7.64 (d, 1H), 7.55 (d, 1H), 7.32 (d, 1H), 6.98 (d, 1H), 5.52 (s, 1H), 4.33 (m, 1H), 4.23 (m, 1H), 3.77 (t, 1H), 3.29 (t, 2H), 2.75 (m, 2H), 1.97 (m, 2H), 1.82 (m, 2H). MS (ES+): M/Z 516 (M+1).

Example 6

Preparation of 5-[3-(6-Bromo-8-chloro-chroman-4-ylamino)-propylamino]-4H-thieno[3,2-b]pyridin-7-one Following the general synthesis procedure described in Example 1 the following compound was prepared. Spectral data confirms the identity of the compound.

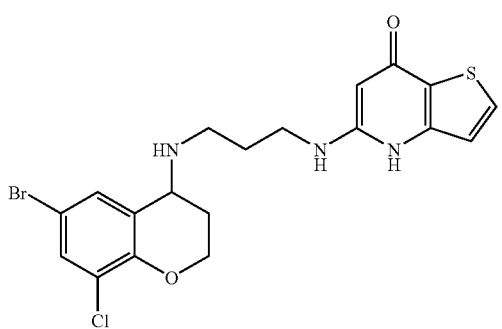

(IX)

$^1$H NMR (400 MHz, CD$_3$OD): δ7.69 (d, 1H), 7.43 (s, 1H), 7.37 (s, 1H), 7.04 (d, 1H), 5.58 (s, 1H), 4.38 (m, 1H), 4.29 (m, 1H), 3.84 (t, 1H), 3.34 (t, 2H), 2.80 (m, 2H), 2.04 (m, 2H), 1.87 (m, 2H). MS (ES+): M/Z 470 (M+1).

Example 7

Preparation of 5-[3-(6-Bromo-8-chloro-1,2,3,4-tetrahydro-quinolin-4-ylamino)-propylamino]-4H-thieno[3,2-b]pyridin-7-one Following the general synthesis procedure described in Example 1 the following compound was prepared. Spectral data confirms the identity of the compound.

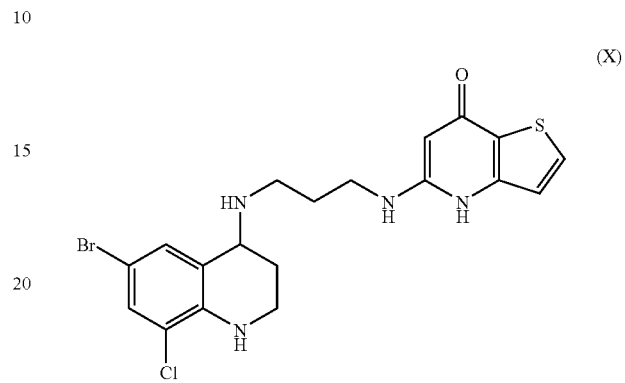

(X)

$^1$H NMR (400 MHz, CD$_3$OD): δ7.69 (d, 1H), 7.22 (s, 1H), 7.21 (s, 1H), 7.03 (d, 1H), 5.57 (s, 1H), 3.78 (t, 1H), 3.45-3.33 (m, 4H), 2.80 (m, 2H), 2.03 (m, 1H), 1.90-1.79 (m, 3H). MS (ES+): M/Z 469 (M+1).

Example 8

Preparation of 5-[3-(8-Bromo-6-chloro-1,2,3,4-tetrahydro-quinolin-4-ylamino)-propylamino]-4H-thieno[3,2-b]pyridin-7-one Following the general synthesis procedure described in Example 1 the following compound was prepared. Spectral data confirms the identity of the compound.

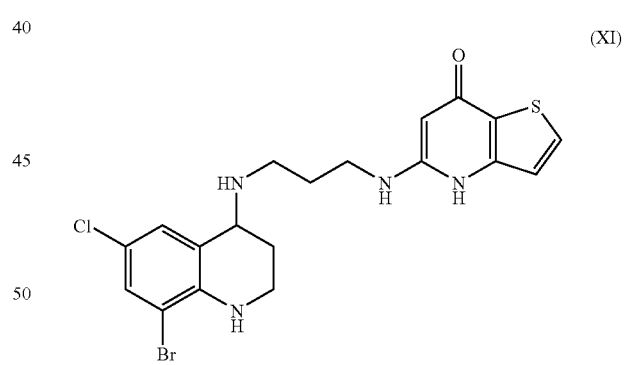

(XI)

$^1$H NMR (400 MHz, CD$_3$OD): δ7.69 (d, 1H), 7.27 (s, 1H), 7.13 (s, 1H), 7.03 (d, 1H), 5.57 (s, 1H), 3.79 (br s, 1H), 3.50-3.33 (m, 4H), 2.82 (m, 2H), 2.04 (m, 1H), 1.92-1.78 (m, 3H). MS (ES+): M/Z 469 (M+1).

Example 9

Preparation of 5-[3-(8-Bromo-6-methylsulfanyl-chroman-4-ylamino)-propylamino]-4H-thieno[3,2-b]pyridin-7-one Following the general synthesis procedure described in Example 1 the following compound was prepared. Spectral data confirms the identity of the compound.

(XII)

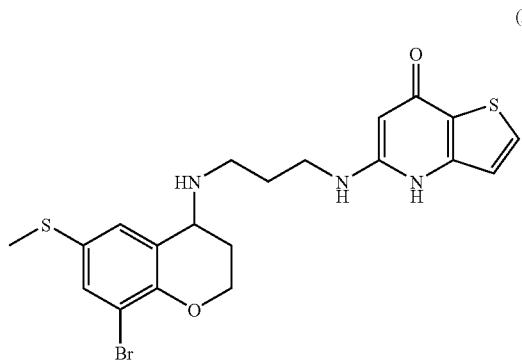

¹H NMR (400 MHz, CD₃OD): δ 7.70 (d, 1H), 7.36 (s, 1H), 7.30 (s, 1H), 7.02 (d, 1H), 5.58 (s, 1H), 4.38 (m, 1H), 4.28 (m, 1H), 3.86 (t, 1H), 3.35 (t, 2H), 2.82 (m, 2H), 2.38 (s, 3H), 2.05 (m, 2H), 1.88 (m, 2H). MS (ES+): M/Z 481.7 (M+1).

Example 10

Preparation of 5-[3-(6-Bromo-8-fluoro-1,2,3,4-tetrahydro-quinolin-4-ylamino)-propylamino]-4H-thieno[3,2-b]pyridin-7-one Following the general synthesis procedure described in Example 1 the following compound was prepared. Spectral data confirms the identity of the compound.

(XIII)

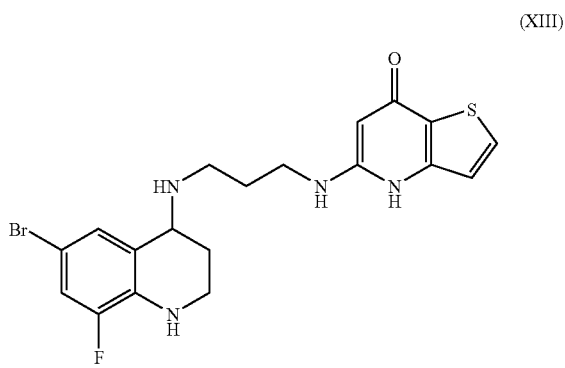

¹H NMR (400 MHz, CD₃OD): δ7.69 (d, 1H), 7.11 (s, 1H), 7.03 (d, 1H), 7.00 (d, 1H), 5.57 (s, 1H), 3.79 (br s, 1H), 3.40-3.33 (m, 4H), 2.82 (m, 2H), 2.04 (m, 1H), 1.92-1.78 (m, 3H). MS (ES+): M/Z 452 (M+1).

Example 11

Preparation of 2-[3-(6,8-Dibromo-1-benzothiopyran-4-ylamino)-proplamino]-1H-quinolin-4-one Following the general synthesis procedure described in Example 1 the following compound was prepared. Spectral data confirms the identity of the compound.

(XIV)

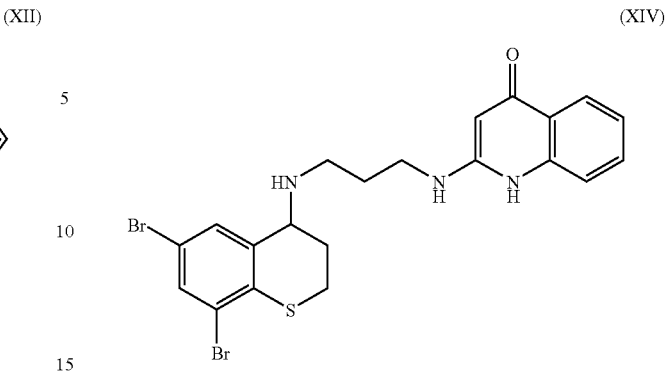

¹H NMR (400 MHz, CD₃OD): δ8.06 (d, 1H), 7.51 (m, 3H), 7.32 (d, 1H), 7.22 (d, 1H), 5.65 (s, 1H), 3.83 (bs, 1H), 3.39 (t, 2H), 2.97 (m, 1H), 2.77 (m, 2H), 2.34 (m, 1H), 1.86 (m, 4H).

Example 12

Expression and Purification of MetRS

The following Example illustrates expression and purification of *C. difficile* MetRS useful in the functional assays shown in Examples 13, 14 and 15.

Cloning of Over-producing Vector: N-terminally hexaHistagged *C. difficile* MetRS was amplified and cloned into pETcoco-2. The following primers were used to amplify DNA from genomic DNA: 5'-CTGCAGAGCTAGCAAAC-CGAGTTTTTATGTAAC-3' (forward) (SEQ ID NO:1), 5'-CTTTCTAAGCTTCTACTAACGAACCTCGGATCC-3' (reverse) (SEQ ID NO:2). Amplified DNA was treated with Sph1 and HindIII restriction endonucleases, which were heat-inactivated after digestion. The fragment was ethanol-precipitated and combined with pETcoco-2 vector (Novagen) that had been treated with the same enzymes plus shrimp alkaline phophatase. The fragments were ligated and the ligation mixture transformed into competent DH10 *E. coli*. Transformants were plated on F-medium plus glucose with 50 ug/ml ampicillin. Growth in glucose maintains the repressed state of the pBAD promoter driving expression of the replicator TrfA, thus maintaining low copy number. The resulting expression clone, pETcoco-Cdiff-MRS, was confirmed by sequencing of the insert in both directions.

Purification of *C. difficile* MetRS. The expression vector pETcoco-Cdiff-MRS was transformed into Rosetta DE3 expression strain and used to inoculate 4 liters of F media supplemented with 10 ug/mL chloramphenicol, 50 ug/mL ampicillin, 0.2% glucose. The culture was induced with 1 mM IPTG at OD 0.66. Cells were harvested 4 hours post-induction (yield=38 g cell pellet). Pelleted cells were lysed by adding 78 g of a 1:1 suspension of frozen cells (39 g cells) in Tris-sucrose which had been stored at −20° C. to 107.25 ml Tris-sucrose buffer that had been pre-warmed to 45° C. (2.75 ml/g of cells). To the stirred mixture, 1.95 ml of 0.5M 1,4-dithiothreitol (DTT) (0.05 ml/g of cells) and 9.75 ml of lysis buffer (2M NaCl, 0.3M spermidine in Tris-sucrose adjusted to pH 7.5) (0.25 ml/g of cells) was added. The pH of the slurry was tested with pH paper and adjusted to pH 8.0 by the addition of 50 ml of 2 M Tris base. Lysozyme (117 mg) was added in 20 ml of Tris-sucrose buffer (3 mg lysozyme/g of cells). The slurry was distributed into centrifuge bottles and incubated at 4° C. for 1 hour followed by incubation at 37° C. for 4 minutes. The insoluble cellular components were removed by centrifugation (23,000×g, 60 min, 4° C.). The recovered supernatant (192 ml) constituted Fraction I. Fraction I was loaded onto a 15 mL Ni-NTA column which was equilibrated in Load Buffer (50 mM Tris-HCl, pH 7.5, 10% glycerol, 40 mM KCl, 10 mM Imidazole, pH 6.8, and 7 mM beta mercaptoethanol). The column was washed with 10 column volumes of Wash Buffer (50 mM Tris-HCl, pH 7.5, 10% glycerol, 800 mM KCl, 20 mM Imidazole, pH 6.8, and 7 mM beta mercaptoethanol). The protein was eluted in 10 column volume gradient from Wash Buffer to Elution Buffer (50 mM Tris-HCl, pH 7.5, 10% glycerol, 40 mM KCl, 250 mM Imidazole, pH 6.8, and 7 mM beta mercaptoethanol) at 0.5 mL/min collecting 3 mL fractions. Fractions were collected and analyzed for protein by SDS-PAGE. Fractions were assayed in the *C. difficile* MetRS tRNA charging assay. Fractions containing peak activity were pooled to form Fraction II (60 mg at 1.3 mg/ml). Fraction II had a specific activity of $3.2 \times 10^5$ units per mg. The purity was estimated at greater than 97% based on densitometry of an SDS-PAGE gel stained with Coomassie blue.

Example 13

Compounds of the Present Invention Have Potent Activity Against MetRS Enzymes

Compounds of the present invention may be assayed to determine their ability to inhibit enzyme MetRS, using recombinant MetRS as follows:

| Reaction Mix (per 1 ml) | | |
| --- | --- | --- |
| Stock | Volume (µl) | Final Concentration |
| 100 mM Tris/Cl, pH 7.9 | 600 | 30 mM |
| 250 mM KCl | | 75 mM |
| 125 mM ATP | 40 | 2.5 mM |
| 250 mM MgCl$_2$ | 80 | 10 mM |
| 50 mM DTT | 80 | 2 mM |
| 1 mM Met (H-3 hot and cold) | 20 | 10 µM |
| Solid tRNA (Mixed *E. coli* MRE 600) | 4 mg/ml | 2 mg/ml |
| H$_2$O | 180 | |

10× Inhibitor (0-100 µM) 5 µl per well 0-10 µM

The reaction is started by adding 20 µl appropriately diluted pure enzyme (pre-incubated with inhibitor) to 25 µl reaction mix for 10 min at room temperature. The reaction is terminated by the addition of 150 µl 167 mM sodium citrate, pH 2.15 containing phosphodiesterase (PDE) SPA beads (0.833 mg/ml). The binding of the radiolabelled product to the bead brings the isotope into close enough proximity to allow radiation from the tritium to excite the scintillant within the bead. Any unbound radiolabel is not close enough to the scintillant to allow this energy transfer, so no signal is generated. Following termination of the reaction, plates are spun at 2500 rpm for 5 min in a Mistral 3000E plate centrifuge (or alternatively allowed to stand for 1 hour). The assay is conducted in 96-well Optiplates (Packard). Plates are counted on a TopCount. (Packard 96 well counter).

Reagents: Mixed *E. coli* MRE 600 tRNA and ATP were purchased from Boehringer-Mannheim, L-[methyl-$^3$H]methionine and phosphodiesterase scintillation proximity (SPA) beads from Amersham Pharmacia Biotech and other reagents from Sigma.

Results: Data indicates that compounds of the invention have IC$_{50}$ values against MetRS in the range <1.5 to 100 nM. All are highly selective with respect to the mammalian enzyme (no inhibition of rat MetRS up to 1 µM). MetRS inhibitors are competitive inhibitors of methionine and uncompetitive inhibitors of ATP.

Example 14

Compounds of the Present Invention Have Potent Antibacterial Activity Against *C. difficile*

Compounds of the present invention may be also assayed for their capacity to inhibit *C. difficile* growth. MIC$_{90}$ (minimum inhibition concentration required to inhibit the growth of 90% of *C. difficile*) was determined using standard agar based assays.

Organisms: All compounds were tested for antibacterial activity against a collection of non-repeat clinical isolates of *C. difficile*. The organisms were stored frozen in Brucella broth supplemented with 20% glycerol. The organisms were retrieved from the freezer and subcultured twice onto CDC agar to ensure purity and growth. The plates were incubated under anaerobic conditions for at least 24 hours. Bacterial colonies were examined for morphology; yellow color, ground glass texture and characteristic odor. The control organism tested was *Bacteroides fragilis* ATCC 25285.

Antimicrobial susceptibility testing: Antimicrobial susceptibility testing was conducted by the agar dilution method on Brucella agar supplemented with vitamin K$_1$, hemin and 5% laked sheep blood in accordance with CLSI guidelines (CLSI, M11-A2). The test compounds were serially diluted and added to molten supplemented Brucella agar. Drug free plates were inoculated before and after inoculation of each antimicrobial plate series and were used as growth controls. Anaerobic/aerobic growth controls were conducted on drug free plates after two sets of drug plates. Bacterial colonies were suspended in Brucella broth to a turbidity equal to that of a 0.5 McFarland standard and applied to a plate with a Steers replicator that delivered 10$^5$ CFU/spot. The plates were incubated under anaerobic conditions for 24 hours at 35° C. prior to the reading of the results. The minimum inhibitory concentration (MIC) was the concentration that completely inhibited growth or caused a marked reduction in the appearance of growth compared to that of the drug-free growth control.

Results: The MIC$_{90}$'s of the compounds illustrated in the examples range from 0.5-8 µg/ml. These results indicate the potent activity of the compounds of the present invention against *C. difficile*, typically around 1.0 µg/ml. In addition, IC$_{50}$ data indicates that the compounds of the present invention are specific for *C. difficile*, showing little or no activity against mammalian MetRS. MetRS inhibitor compounds show potent activity against *C. difficile* and Gram-positive aerobic bacteria while sparing normal gut flora.

Example 15

Compounds of the Present Invention Have Potent Antibacterial Activity Against other Bacteria Compounds of the present invention were tested for antibacterial activity against a panel of Gram-positive bacteria. Compounds were tested against Gram-positive aerobic bacteria using the CLSI-reference broth microdilution method. Data was obtained against *S. aureus, E. faecalis, E. faecium, S. pyogenes, S. epidermidis* and *S. haemolyticus*. The compounds tested demonstrated potent antibacterial activity against all isolates with a MIC range of <0.008-8 µg/ml, including resistant strains of *S. aureus, S. epidermidis* and *S.*

*pyogenes.* Data was also obtained against Helicobacter, *H. pylori* using the standard CLSI guideline agar dilution method and results indicate that the compounds of the invention are active against *H. pylori.*

The data illustrated the utility of using the compounds of the present invention as antibacterial agents against other Gram-positive bacteria, e.g., *S. aureus, E. faecalis, E. faecium S. pyogenes, S. epidermidis,* and *S. haemolyticus* and against the Gram-negative bacteria *H. pylori.*

Example 16

Compounds of the Present Invention Show Strong Therapeutic Utility During in vivo Trials Animal studies were performed to determine the efficacy of MetRS inhibitors for treating *C. difficile*-infections. The MetRS inhibitors tested were 5-[3-((R)-6,8-Dibromo-chroman-4-ylamino)-propylamino]-4H-thieno[3,2-b]pyridine-7-one (both racemic mixture and the R enantiomer) and 5-[3-((R)-8-Bromo-6-chloro-chroman-4-ylamino)-propylamino]-4H-thieno[3,2-b]pyridin-7-one. Also tested was 2-(3-{3,5-Dibromo-2-[2-(4-methyl-thiazol-5-yl)-ethoxy]-benzylamino}-propylamino)-1H-quinolin-4-one.

Results were compared to *C. difficile*-infected hamsters treated with the conventional antibiotic, vancomycin. Infected hamsters were treated with either a solution or suspension of a MetRS inhibitor at 5 to 50 mg/kg or vancomycin at 2.5, 5 or 25 mg/kg. There were eight hamsters per group with the final endpoint of the experiment being survival. Expired hamsters were examined for GI condition.

Data for the studies indicated that control hamsters (infected with *C. difficile* but receiving no treatment) died within 3-4 days. Hamsters treated with MetRS inhibitors showed a significant increase in survival, often living until study termination, typically 28 or more days. These results were similar or superior to the results obtained using vancomycin treatment. 5-[3-((R)-6,8-Dibromo-chroman-4-ylamino)-propylamino]-4H-thieno[3,2-b]pyridine-7-one demonstrated the best efficacy. 5-[3-((R)-6,8-Dibromo-chroman-4-ylamino)-propylamino]-4H-thieno[3,2-b]pyridine-7-one exhibited superior efficacy to vancomycin in that >60% survival was observed on Day 28 (5 mg/kg BID) as compared to 0-10% survival with vancomycin. Surviving animals had healthy GI appearance and histopathology. Low systemic exposure and bioavailability was observed in hamsters following oral administration of the MetRS inhibitors.

The data in this Example illustrates that the compounds of the present invention were comparable or superior to vancomycin in their capability to treat animals infected with *C. difficile.*

Example 17

Compounds of the Present Invention Effect Toxin Production in *C. difficile*

The pathogenicity of *C. difficile* is associated with its ability to produce the extracellular toxins A and B. Hypertoxinogenic strains are responsible for recent outbreaks with high mortality. In contrast, isolates that do not produce toxins are non-pathogenic. Since toxin production requires active protein synthesis, inhibition of the protein synthesis machinery is expected to suppress de novo toxin production. Therefore, MetRS inhibitors were evaluated for their effect on *C. difficile* toxin production in vitro.

Methods:

*C. difficile* strain ATCC43255 was grown and maintained anaerobically on CDC anaerobe agar (Remel, Lenexa, Kans.). To test the effect of antibacterial agents on growth, cells were grown anaerobically for 40 h at 35° C. in 96-well brain heart infusion (BHI) broth cultures, with an initial inoculum of $10^6$ CFU/mL. To test the effect of antibacterial agents on toxin production at high *C. difficile* cell densities, the cells were grown anaerobically for 24 h at 35° C. in 96-well brain heart infusion (BHI) broth cultures. Spent medium was then replaced with fresh broth containing MetRS inhibitors and control agents at a concentration range of 0.015-16 µg/mL. After 4 days, growth and cell viability were monitored by optical density measurements at 595 nm and by culture on CDC anaerobe agar, respectively. Culture supernatants were collected, and toxin A was detected by ELIFA (enzyme-linked immuno-flow assay) using an anti toxin A monoclonal antibody (Novus Biologicals, Centennial, Colo.).

Results:

The MetRS inhibitors 5-[3-(6,8-Dibromo-chroman-4-ylamino)-propylamino]-4H-thieno[3,2-b]pyridin-7-one and 5-(3-{3,5-Dibromo-2-[2-(4-methyl-thiazol-5-yl)-ethoxy]-benzylamino}-propylamino)-4H-thieno[3,2-b]pyridin-7-one prevented growth of *C. difficile* in broth at concentrations of $\geq$0.25 µg/mL.

Toxin production in high cell density, 4 day old stationary phase cultures was inhibited by four different MetRS inhibitors (5-[3-(6,8-Dibromo-chroman-4-ylamino)-propylamino]-4H-thieno[3,2-b]pyridin-7-one, 5-(3-{3,5-Dibromo-2-[2-(4-methyl-thiazol-5-yl)-ethoxy]-benzylamino}-propylamino)-4H-thieno[3,2-b]pyridin-7-one, R-(+)-5-[3-(6,8-Dibromo-chroman-4-ylamino)-propylamino]-4H-thieno[3,2-b]pyridin-7-one di-hydrochloride, 5-[3-(6,8-Dibromo-1,2,3,4-tetrahydro-quinolin-4-ylamino)-propylamino]-4H-thieno[3,2-b]pyridin-7-one tri-hydrochloride) at concentrations as low as 0.25 µg/mL. In contrast, much higher concentrations (4->16 µg/mL) of the comparator agents (metronidazole, vancomycin, levofloxacin) were required to inhibit toxin production.

Conclusions:

MetRS inhibitors demonstrate inhibitory effects on both growth and toxin production of *C. difficile* in broth cultures. Furthermore, toxin production was effectively blocked in stationary phase cultures. As a consequence of this suppression of toxin production by bacteriostatic MetRS inhibitors, *C. difficile* becomes essentially non-toxinogenic and thus non-pathogenic. This effect is unique to protein synthesis inhibitors, such as MetRS inhibitors, whose mode-of-action does not require that the bacteria are actively growing.

Example 18

Compounds of the Present Invention Effect Spore Production in *C. difficile*

*C. difficile* is an organism well known for its ability to form spores that are resistant to heating, drying and many cleaning agents such as disinfectants. Spores present in the environment may serve as a reservoir for disease-causing organisms. *C. difficile* infections are often initiated by the ingestion of spores that germinate in the GI tract causing CDAD. Spore retention in the gut after treatment for CDAD is also thought to be a major source of relapsing disease. Reduction in the capacity of *C. difficile* to produce spores or spore germination could represent an important breakthrough in the treatment of this disease. Spore coats are composed primarily of protein, generation of the spore coat requires protein synthesis and inhibition of active protein synthesis is expected to affect spore production in this organism. Therefore, MetRS inhibitors were evaluated for their effect on C. difficile spore production in vitro.

Methods:

MetRS inhibitors were evaluated for their effect on sporulation of four clinical isolates of C. difficile, including two recent outbreak isolates that belong to the BI/NAP1 genotype. C. difficile strains were grown on supplemented Brucella blood for 24 to 48 hours and colonies suspended in saline to achieve a turbidity equivalent to a 0.5 McFarland standard. C. difficile suspensions (10 µL) were spread onto the surface of fresh supplemented Brucella agar plates with 5% laked sheep blood containing MetRS inhibitors at concentrations ranging from 0.06 to 2 µg/mL and incubated anaerobically at 35° C. for 96 hours. Aliquots of the same cell suspensions used to inoculate the MetRS containing plates were also plated for viable counts and an additional 250 µL aliquot was treated with 250 µL of absolute ethanol for 1 hour at room temperature to eliminate vegetative cells and permit the enumeration of spores. The ratio of spores to total cells was again determined for all four strains after 96 hours of incubation in the presence of compound and used to compare the effects of MetRS inhibitors with drug free controls on sporulation rates.

Results:

Three out of four C. difficile strains produced measurable number of spores and were evaluated as described above. Treatment of all strains with 5-[3-((R)-6,8-Dibromo-chroman-4-ylamino)-propylamino]-4H-thieno[3,2-b]pyridine-7-one in all strains showed reductions in spore production at 0.25×MIC (<2% spores) and at 0.5×MIC (<1% spores). This is in marked contrast to the results obtained after treatment with metronidazole, where all tested strains display marked increases in spore production (up to 100% spores) after exposure to subMIC concentrations of the drug. Treatment with vancomycin induced similar spore production increases in two strains but not in one strain where the spore counts remained low.

Conclusions:

5-[3-((R)-6,8-Dibromo-chroman-4-ylamino)-propylamino]-4H-thieno [3,2-b]pyridine-7-one at subMIC (0.25 and 0.5×MIC) was effective in preventing vegetative cells of C. difficile from forming spores. These data suggest that 5-[3-((R)-6,8-Dibromo-chroman-4-ylamino)-propylamino]-4H-thieno[3,2-b]pyridine-7-one might also have a useful role in preventing outbreaks and reducing relapse rates that have been correlated with widespread prevalence of C. difficile spores in the environment.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims.

What is claimed is:

1. A compound of formula (I):

(I)

in which:

$R^1$ is selected from halo, cyano, hydroxyl, $(C_{1-6})$alkyl (optionally substituted by halo, hydroxyl, amino, mono to perfluoro$(C_{1-3})$alkyl, carboxy, or $(C_{1-6})$alkoxycarbonyl), $(C_{3-7})$cycloalkyl, $(C_{1-6})$alkoxy, amino, mono- or di-$(C_{1-6})$alkylamino, acylamino, carboxy, $(C_{1-6})$alkoxycarbonyl, carboxy($C_{1-6}$)alkyloxy, ($C_{1-6}$)alkylthio, ($C_{1-6}$) alkylsulphinyl, ($C_{1-6}$)alkylsulphonyl, sulphamoyl, mono- and di($C_{1-6}$)alkylsulphamoyl, carbamoyl, mono- and di-($C_{1-6}$)alkylcarbamoyl, and heterocyclyl;

Y is a linker group having from one to six methylene groups in a straight chain and in which one or more methylene groups may have one or more ($C_{1-6}$) alkyl, ($C_{1-6}$)alkoxy or ($C_{1-6}$)alkylidenyl substituents;

$R^2$ is selected from halo, cyano, hydroxyl, ($C_{1-6}$)alkyl (optionally substituted by halo, hydroxyl, amino, mono to perfluoro($C_{1-3}$)alkyl, carboxy, or ($C_{1-6}$)alkoxycarbonyl), ($C_{3-7}$)cycloalkyl, ($C_{1-6}$)alkoxy, amino, mono- or di-($C_{1-6}$)alkylamino, acylamino, carboxy, ($C_{1-6}$)alkoxycarbonyl, carboxy($C_{1-6}$)alkyloxy, ($C_{1-6}$)alkylthio, ($C_{1-6}$) alkylsulphinyl, ($C_{1-6}$)alkylsulphonyl, sulphamoyl, mono- and di($C_{1-6}$)alkylsulphamoyl, carbamoyl, mono- and di-($C_{1-6}$)alkylcarbamoyl, and heterocyclyl;

when $Z_1$ is S, $Z_2$ and $Z_3$ are CH; when $Z_2$ is S, $Z_1$ and $Z_3$ are CH; when $Z_3$ is S, $Z_1$ and $Z_2$ are CH;

X is NH, S, SO, $SO_2$, O or $CH_2$;

n is one, two or three; and m is 0 or an integer from 1 to 4.

2. A compound of claim 1 having a formula (II):

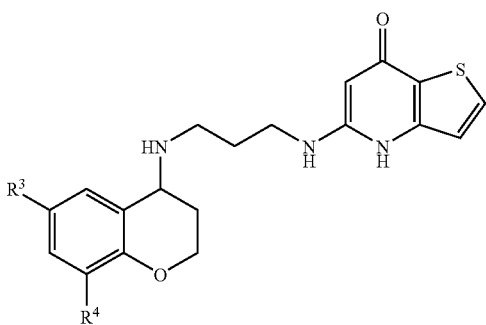

in which:
R³ and R⁴ can be the same or a different substituent and are selected from halo, cyano, hydroxyl, ($C_{1-6}$)alkyl (optionally substituted by halo, hydroxyl, amino, mono to perfluoro($C_{1-3}$)alkyl, carboxy, or ($C_{1-6}$) alkoxycarbonyl), ($C_{3-7}$)cycloalkyl, ($C_{1-6}$)alkoxy, amino, mono- or di-($C_{1-6}$)alkylamino, acylamino, carboxy, ($C_{1-6}$)alkoxycarbonyl, carboxy($C_{1-6}$)alkyloxy, ($C_{1-6}$)alkylthio, ($C_{1-6}$)alkylsulphinyl, ($C_{1-6}$) alkylsulphonyl, sulphamoyl, mono- and di($C_{1-6}$) alkylsulphamoyl, carbamoyl, mono- and di-($C_{1-6}$) alkylcarbamoyl, and heterocyclyl.

3. A compound of claim 1 having a formula (III):

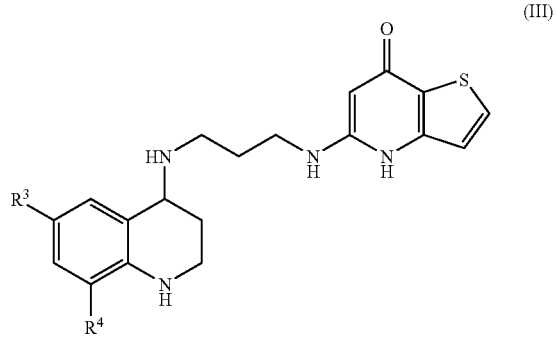

in which:
R³ and R⁴ can be the same or a different substituent and are selected from halo, cyano, hydroxyl, ($C_{1-6}$)alkyl (optionally substituted by halo, hydroxyl, amino, mono to perfluoro($C_{1-3}$)alkyl, carboxy, or ($C_{1-6}$) alkoxycarbonyl), ($C_{3-7}$)cycloalkyl, ($C_{1-6}$)alkoxy, amino, mono- or di-($C_{1-6}$)alkylamino, acylamino, carboxy, ($C_{1-6}$)alkoxycarbonyl, carboxy($C_{1-6}$)alkyloxy, ($C_{1-6}$)alkylthio, ($C_{1-6}$)alkylsulphinyl, ($C_{1-6}$) alkylsulphonyl, sulphamoyl, mono- and di($C_{1-6}$) alkylsulphamoyl, carbamoyl, mono- and di-($C_{1-6}$) alkylcarbamoyl, and heterocyclyl.

4. The salt of the compound of claim 1, wherein the salt is a pharmaceutically acceptable salt.

5. A compound of formula (I) as claimed in claim 1 selected from:
   5-[3-(6,8-Dibromo-1,2,3,4-tetrahydro-quinolin-4-ylamino)-propylamino]-4H-thieno[3,2-b]pyridin-7-one;
   5-[3-(6,8-Dibromo-chroman-4-ylamino)-propylamino]-4H-thieno[3,2-b]pyridin-7-one;
   5-[3-(8-Bromo-6-chloro-chroman-4-ylamino)-propylamino]-4H-thieno[3,2-b]pyridin-7-one;
   5-[3-(6-Chloro-8-iodo-chroman-4-ylamino)-propylamino]-4H-thieno[3,2-b]pyridin-7-one;
   5-[3-(6-Bromo-8-chloro-chroman-4-ylamino)-propylamino]-4H-thieno[3,2-b]pyridin-7-one;
   5-[3-(6-Bromo-8-chloro-1,2,3,4-tetrahydro-quinolin-4-ylamino)-propylamino]-4H-thieno[3,2-b]pyridin-7-one;
   5-[3-(8-Bromo-6-chloro-1,2,3,4-tetrahydro-quinolin-4-ylamino)-propylamino]-4H-thieno[3,2-b]pyridin-7-one;
   5-[3-(8-Bromo-6-methylsulfanyl-chroman-4-ylamino)-propylamino]-4H-thieno[3,2-b]pyridin-7-one; and
   5-[3-(6-Bromo-8-fluoro-1,2,3,4-tetrahydro-quinolin-4-ylamino)-propylamino]-4H-thieno[3,2-b]pyridin-7-one.

6. A pharmaceutical composition comprising an antibacterially effective amount of a compound according to claim 1 together with a pharmaceutically accepted carrier or excipient.

* * * * *